United States Patent [19]

Faustino et al.

[11] Patent Number: 4,868,170
[45] Date of Patent: Sep. 19, 1989

[54] STERIOD LOTION FORMULATION

[75] Inventors: Marilia M. Faustino, Spotswood; Sailesh A. Varia, Plainsboro, both of N.J.; Abu T. M. Serajuddin, Flushing, N.Y.

[73] Assignee: E. R. Squibb & Sons, Inc., Princeton, N.J.

[21] Appl. No.: 120,277

[22] Filed: Nov. 13, 1987

[51] Int. Cl.$^4$ .............................................. A61K 31/56
[52] U.S. Cl. ................... 514/179; 514/177; 514/178; 514/180
[58] Field of Search ............... 514/169, 170–179, 514/180–182, 937–941, 943, 944, 947, 969, 970, 973

[56] References Cited

U.S. PATENT DOCUMENTS

| 2,801,202 | 7/1957 | Poetsch | 514/171 |
| 3,670,080 | 6/1972 | Hirata | 514/172 |
| 3,856,954 | 12/1974 | Jackson | 514/174 |
| 4,048,310 | 9/1977 | Chen et al. | 514/174 |
| 4,071,620 | 1/1978 | Sklar | 514/226.2 |
| 4,344,940 | 8/1982 | Chow et al. | 514/177 |
| 4,436,738 | 3/1984 | Bequette et al. | 514/182 |

OTHER PUBLICATIONS

Aldrich Catalog of Fine Chemicals (Aldrich Chemical Company) 1988, p. 1516.

Primary Examiner—H. M. S. Sneed
Assistant Examiner—J. Saba
Attorney, Agent, or Firm—Burton Rodney

[57] ABSTRACT

A steroid lotion formulation which has enhanced physical and chemical stability is formed of (11$\beta$,17$\alpha$)-17-(ethylthio)-9$\alpha$-fluoro-11$\beta$-hydroxy-17-(methylthio)androsta-1,4-diene-3-one (tipredane), and a vehicle containing as major ingredients polyethylene glycol, propylene glycol and water together with a potassium citrate buffer or tromethamine buffer, and sodium metabisulfite and butylated hydroxytoluene as antioxidants.

9 Claims, No Drawings

STERIOD LOTION FORMULATION

FIELD OF THE INVENTION

The present invention relates to a steroid lotion formulation which has enhanced physical and chemical stability and contains (11$\beta$,17$\alpha$)-17-(ethylthio)-9$\alpha$-fluoro-11$\beta$-hydroxy-17-(methylthio)-androsta-1,4-dine-3-one (tipredane) as the active ingredient.

BACKGROUND OF THE INVENTION

U.S. Pat. No. 4,361,559 to Varma discloses antinflammatory 17,17-bis(substituted thio) androstenes of the formula

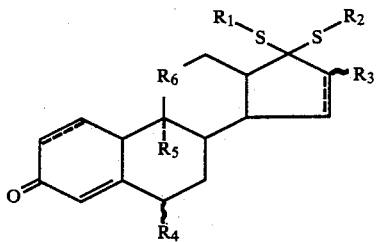

wherein
$R_1$ and $R_2$ are the same or different and each is alkyl, cycloalkyl or aryl;
$R_3$ is hydrogen, hydroxy, alkoxy, aryloxy, alkylthio, arylthio,

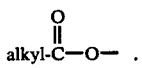

or halogen;
$R_4$ is hydrogen, methyl, hydroxy,

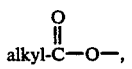

or halogen;
$R_5$ is hydrogen or halogen; and
$R_6$ is carbonyl or $\beta$-hydroxymethylene. A broken line in the 1,2-, 6,7- and 15,16-position of a structural formula indicates the optional presence of ethylenic unsaturation.

Included among the compounds covered in the Varma patent is tipredane which has been found to be a highly effective topical antiinflammatory agent.

Tipredane is practically insoluble in water (less than 0.0002 mg/ml at 25° C.); 1:1 hydroalcoholic mixtures of tipredane are unstable under acidic conditions. Furthermore, tipredane itself is susceptible to oxidation. Where it has been attempted to formulate tipredane with a sodium metabisulfite anti-oxidant and a potassium buffer, it has been found that sulfate was formed by the oxidation of metabisulfite. Furthermore, the presence of excess potassium ion in the formulation could lead to the precipitation of potassium sulfate crystals.

Until now, attempts to prepare a stable lotion formulation containing tipredane which overcomes the above stability problems have not been successful.

DESCRIPTION OF THE INVENTION

In accordance with the present invention, a topical steroid lotion formulation is provided which contains the steroid tipredane as its active ingredient and has excellent physical and chemical stability. The lotion formulation according to the present invention contains in addition to tipredane, a carrier vehicle which is formed of polyethylene glycol, propylene glycol and water and contains a buffer to maintain the lotion pH from about 5 to about 8, such as potassium citrate, preferably in the form of the monohydrate, or tromethamine, an antioxidant such as sodium metabisulfite and an auxiliary antioxidant such as butylated hydroxytoluene, and a metal chelating agent such as dipotassium ethylene diamine tetraacetic acid preferably in the form of the dihydrate.

The tipredane steroid will be present in an amount within the range of from about 0.005 to about 0.15% by weight and preferably from about 0.05 to about 0.1% by weight based on the total weight of the formulation.

The carrier or vehicle will include polyethylene glycol in an amount within the range of from about 62 to about 70% by weight and preferably from about 65 to about 67% by weight of the total lotion formulation. The polyethylene glycol

will have an n value of from about 350 to about 500.

Propylene glycol will be present in an amount within the range of from about 10 to about 20% by weight and preferably from about 10 to about 15% by weight of the lotion formulation.

In addition, water will be present in an amount within the range of from about 15 to about 25% and preferably from about 18 to about 22% by weight of the total lotion formulation.

An important feature of the lotion formulation of the invention is its excellent chemical stability and physical stability so that potassium sulfate crystals will not precipitate out even after extended periods of storage. This is achieved due to the presence of potassium citrate as a buffer in an amount within the range of from about 0.2 to about 0.5% by weight and preferably from about 0.2 to about 0.3% by weight, or the presence of tromethamine as a buffer in an amount within the range of from about 0.2 to about 1% by weight and preferably from about 0.3 to about 0.7% by weight, and sodium metabisulfite present as an antioxidant in an amount within the range of from about 0.005 to about 0.03% by weight and preferably from about 0.01 to about 0.02% by weight of the lotion formulation.

In order to maintain proper pH of within the range of from about 5 to about 8, the lotion formulation may include an acid such as hydrochloric acid, sulfuric acid or phosphoric acid in an amount to bring the lotion to the required pH. The acid will normally be present when tromethamine is employed as the buffer.

The auxiliary antioxidant will be present in an amount within the range of from about 0.01 to about 1% by weight and preferably from about 0.03 to about 0.07% by weight of the lotion.

Examples of antioxidants which may be employed include butylated hydroxytoluene, butylated hydroxyanisole, propyl gallate or sodium ascorbate.

As the metal chelating agent, dipotassium ethylenediamine tetraacetate dihydrate is preferred. The metal chelating will be employed in an amount within the range of from about 0.001 to about 0.01% by weight and preferably from about 0.003 to about 0.006% by weight of the lotion formulation.

The following represents preferred lotion formulations in accordance with the present invention.

| Ingredient | Range Percent w/w | | | Range Percent w/w | | |
|---|---|---|---|---|---|---|
| Tipredane | 0.05 | to | 0.15 | 0.05 | to | 0.15 |
| Polyethylene glycol 400 | 65 | to | 67 | 65 | to | 67 |
| Propylene glycol | 10 | to | 15 | 10 | to | 15 |
| Potassium citrate monohydrate | 0.2 | to | 0.3 | | | |
| Sodium metabisulfite | 0.01 | to | 0.02 | 0.01 | to | 0.02 |
| Dipotassium EDTA dihydrate | 0.003 | to | 0.006 | 0.003 | to | 0.006 |
| Butylated hydroxytoluene | 0.03 | to | 0.07 | 0.03 | to | 0.07 |
| Water qs at 100% | 18 | to | 22 | 18 | to | 22 |
| Tromethamine | | | | 0.3 | to | 0.7 |
| Hydrochloric acid | | | | 0.1 | to | 0.5 |

The tipredane lotion formulations of the invention may be prepared as described in the working Examples by simply mixing and dissolving the steroid in the aqueous glycol vehicle base.

The following Examples represent preferred embodiments of the present invention. Unless otherwise indicated, all temperatures are expressed in degrees Centigrade.

EXAMPLE 1

A 0.1% w/w tipredane lotion formulation having the following composition was prepared as described below.

| Tipredane Lotion 0.1 W/W | |
|---|---|
| Ingredient | Percent w/w |
| Tipredane powder | 0.10% |
| Polyethylene glycol 400 N.F. | 65% |
| Propylene glycol U.S.P. | 14% |
| Butylated hydroxytoluene N.F. | 0.05% |
| Potassium citrate monohydrate U.S.P. | 0.25% |
| Dipotassium EDTA (edetate) dihydrate | 0.005% |
| Sodium metabisulfite N.F. | 0.01% |
| Purified water | 20.6% |

Butylated hydroxytoluene (BHT) was weighed and passed through a #20 mesh stainless steel screen. Into a tared 2 liter glass beaker was weighed polyethylene glycol 400 (PEG 400). Propylene glycol was separately weighed and then added to the PEG 400 in the glass beaker. The glycol mixture was stirred and nitrogen was bubbled through the mixture. The glycol mixture was heated to about 75° C. and the batch temperature was maintained between 70° C. to 75° C. for about 30 minutes. The remaining ingredients: tipredane, meshed BHT, dipotassium ethylene diamine tetraacetate (edetate) dihydrate, sodium metabisulfite, potassium citrate and water were separately weighed. The glycol mixture was then allowed to cool to about 50° C. The meshed and weighed BHT was slowly added to the batch which was mixed well to completely dissolve the BHT. The batch was cooled further to a temperature between 25° C. and 35° C. and the weighed tipredane powder was slowly added to the cooled batch. The batch was mixed well to insure complete dissolution of the steroid. The weighed dipotassium edetate dihydrate, sodium metabisulfite and potassium citrate were dissolved in the weighed water. The salt solution was slowly added to the glycol mixture containing tipredane and the batch was mixed well to assure batch homogeneity.

The above tipredane formulation was found to have excellent chemical and physical stability and was free of visible precipitate even after prolonged periods of storage at temperatures of 5° C., 25° C. and 40° C.

EXAMPLE 2

A 0.1% w/w tipredane lotion formulation having the following composition was prepared as described below.

| Tipredane Lotion 0.1 W/W Formulation Using Tromethamine Buffer | |
|---|---|
| Ingredient | Percent w/w |
| Tipredane powder | 0.10% |
| Polyethylene glycol 400 N.F. | 67% |
| Propylene glycol U.S.P. | 14% |
| Butylated hydroxytoluene N.F. | 0.05% |
| Tromethamine U.S.P. | 0.50% |
| Hydrochloric acid, ACS grade | 0.25% |
| Dipotassium edetate dihydrate | 0.005% |
| Sodium metabisulfite N.F. | 0.02% |
| Purified water | 15% |

Butylated hydroxytoluene (BHT) was weighed and passed through a #20 mesh stainless steel screen. Into a tared 2 liter glass beaker was weighed polyethylene glycol 400 (PEG 400). Propylene glycol was separately weighed and then added to the PEG 400 in the glass beaker. The glycol mixture was stirred (magnetic stirring hot plate) and nitrogen was bubbled through the mixture. The glycol mixture was heated to about 75° C. and the batch temperature was maintained between 70° C. to 75° C. for about 30 minutes. The remaining ingredients: tipredane, meshed BHT, dipotassium edetate dihydrate, sodium metabisulfite, tromethamine, hydrochloric acid and water were separately weighed. The glycol mixture was then allowed to cool to about 50° C. The meshed and weighed BHT was slowly added to the glycol mixture which was mixed well to completely dissolve the BHT. The batch was cooled further to a temperature between 25° C. and 35° C. and the weighed tipredane powder was slowly added to the cooled batch. The batch was mixed well to insure complete dissolution of the steroid. The weighed dipotassium edetate dihydrate, sodium metabisulfite, tromethamine and HCl were added to the weighed water and allowed to dissolve with mixing. This salt solution was slowly added to the glycol mixture containing tipredane and the batch was mixed well to assure batch homogeneity.

The above tipredane formulation was found to have excellent chemical and physical stability and was free of visible precipitate even after prolonged periods of storage at temperatures of 5° C., 25° C. and 40° C.

What is claimed is:

1. A lotion formulation having enhanced chemical and physical stability consisting essentially of tipredane in an amount within the range of from about 0.005 to about 0.15%, and a vehicle comprising polyethylene glycol in an amount within the range of from about 62 to about 70%, propylene glycol in an amount within the range of from about 10 to about 20% and water in which said tipredane is soluble in an amount within the range of from about 15 to about 25%, a buffer to maintain a pH of from about 5 to about 8 comprising potassium citrate in an amount to within the range of from about 0.25 to about 0.5% or tromethamine in an amount within the range of from about 0.2 to about 1%, sodium metabisulfite in an amount within the range of from about 0.005 to about 0.03% to be effective as an antioxidant, and a metal chelating agent in an amount within the range of from about 0.001 to about 0.01%, all of the above % being based on the weight of the lotion formulation.

2. The lotion formulation as defined in claim 1 further including butylated hydroxytoluene as an antioxidant.

3. The lotion formulation as defined in claim 1 wherein the a metal chelating agent is dipotassium ethylene diamine tetraacetate dihydrate.

4. The lotion formulation as defined in claim 1 wherein the tipredane is present in an amount within the range of from about 0.05 to about 0.1% by weight, the polyethylene glycol is present in an amount within the range of form about 65 to about 67% by weight, the propylene glycol is present in an amount within the range of from about 10 to about 15% by weight and the water is present in an amount within the range of from about 18 to about 22% by weight, all of the above % being based on the total weight of the lotion formulation.

5. The lotion formulation as defined in claim 1 wherein the buffer is potassium citrate and is present in an amount within the range of from about 0.25 to about 0.3% by weight and sodium metabisulfite is present in an amount within the range of from about 0.005 to about 0.03% by weight.

6. The lotion formulation as defined in claim 1 wherein the buffer is tormethamine and is present in an amount within the range of from about 0.2 to about 1% by weight and sodium metabisulfite is present in an amount within the range of from about 0.005 to about 0.03% by weight and further including hydrochloric acid in an amount within the range of form about 0.1 to about 0.5% by weight.

7. The lotion formulation as defined in claim 1 wherein the polyethylene gylcol has the formula $H(OCH_2OCH_2)_nOH$ wherein n is 300 to 500.

8. The lotion formulation as defined in claim 1 having the formula

|  | % w/w |
|---|---|
| tipredane powder | 0.10% |
| polyethylene glycol 400 | 65% |
| propylene glycol | 14% |
| butylated hydroxytoluene | 0.05% |
| potassium citrate monohydrate | 0.25% |
| dipotassium EDTA dihydrate | 0.005% |
| sodium metabisulfite | 0.01% |
| purified water | 15% |

9. The lotion formulation as defined in claim 1 having the formula

|  | % w/w |
|---|---|
| tipredane powder | 0.10% |
| polyethylene glycol 400 | 67% |
| propylene glycol | 14% |
| butylated hydroxytoluene | 0.05% |
| tromethamine | 0.50% |
| hydrochloric acid | 0.25% |
| dipotassium EDTA dihydrate | 0.005% |
| sodium metabisulfite N.F. | 0.02% |
| purified water | 15% |

* * * * *